United States Patent
Reid et al.

(10) Patent No.: US 7,169,559 B2
(45) Date of Patent: Jan. 30, 2007

(54) LDL RECEPTOR-RELATED PROTEINS 1 AND 2 AND TREATMENT OF BONE OR CARTILAGE CONDITIONS

(75) Inventors: Ian Reginald Reid, Auckland (NZ); Jillian Cornish, Auckland (NZ); Andrew Bevis Grey, Auckland (NZ); Dorit Naot, Auckland (NZ); Kay Patricia Palmano, Palmerston North (NZ)

(73) Assignees: Fonterra Corporate Research and Development Ltd., Wellington (NZ); NZMP + Health and Nutrition Unit, Auckland (NZ); Auckland Uniservices Ltd., Auckland (NZ)

( * ) Notice: Subject to any disclaimer, the term of this patent is extended or adjusted under 35 U.S.C. 154(b) by 471 days.

(21) Appl. No.: 10/436,805

(22) Filed: May 12, 2003

(65) Prior Publication Data

US 2004/0038265 A1 Feb. 26, 2004

Related U.S. Application Data

(60) Provisional application No. 60/463,419, filed on Apr. 16, 2003, provisional application No. 60/380,227, filed on May 13, 2002.

(51) Int. Cl.
C12Q 1/68 (2006.01)
C12Q 1/02 (2006.01)

(52) U.S. Cl. .................................. 435/6; 435/29
(58) Field of Classification Search .............. None
See application file for complete search history.

(56) References Cited

U.S. PATENT DOCUMENTS 6,187,548 B1 * 2/2001 Akerstrom et al. .......... 435/7.2

FOREIGN PATENT DOCUMENTS

| GB | WO 98/46743 | * 10/1998 |
|---|---|---|
| WO | WO 00/76552 | 12/2000 |
| WO | WO 01/57266 | 8/2001 |
| WO | WO 01/92474 | 12/2001 |
| WO | WO/03985 A1 | 1/2002 |
| WO | WO 02/16553 | 2/2002 |
| WO | WO 03/106657 | 12/2003 |
| WO | WO 2004/033657 | 4/2004 |

OTHER PUBLICATIONS

Herz J, "The LDL Receptor Gene Family: (Un)Expected Signal Transducers in the Brain," (Neuron), vol. 29, Mar. 2001, pp. 571-581.*
Gong et al, "LDL Receptor-Related Protein 5 (LRP5) Affects Bone Accrual and Eye Development," (Cell), vol. 107, Nov. 2001, pp. 513-523.*
Kato, M. et al., Apr. 15, 2002, *Cbfal-independent decrease in osteoblast proliferation, osteopenia, and persistent embryonic eye vascularization in mice deficient in Lrp5, a Wnt coreceptor*, Journal of Cell Biology, 157:303-314.
Little, R. D. et al., Jan. 2002, *A mutation in the LDL receptor-related protein 5 gene results in the autosomal dominant high-bone-mass trait*, American Journal of Human Genetics, 70:11-19.
WPI Derwent Database AN 1995-228641 [30]. "Oral composition for treatment of periodontal comprise alpha marco globulin . . . " May 30, 1995, Abstract Only.
Strickland et al. "Diverse roles for the LDL receptor family", Tremds in Endocrinoogy and Metabolism 13(2):66-74, Mar. 2002.
Grey et al. "The low-density lipoprotein receptor-related protein 1 is a mitogenic receptor for lacroferrin in osteoblastic cells", Molecular Endocrinology 18(9):2268-2278, 2004.
Cornish et al. "Lactoferrin and bone: an overview of recent progress". Australian Journal of Dairy Technology 60(1):53-57, 2005.
Niemeier et al. "Identification of megalin/gp330 as a receptor for lipoprotein(a) in vitro". Arteriosclerosis Thrombosis and Vascular Biology 19(3):552-561, Mar. 1999.

* cited by examiner

Primary Examiner—Christopher R. Tate
Assistant Examiner—Amanda P. Wood
(74) Attorney, Agent, or Firm—Fish & Richardson P.C.

(57) ABSTRACT

LDL receptor-related proteins 1 and 2 (LRP-1 and LRP-2) and interaction between lactoferrin and LRP-1, LRP-2, or p42/44 MAP kinase in diagnosis and treatment of disorders such as bone or cartilage disorders. Also disclosed are methods of screening for related therapeutic compounds.

8 Claims, No Drawings

LDL RECEPTOR-RELATED PROTEINS 1 AND 2 AND TREATMENT OF BONE OR CARTILAGE CONDITIONS

RELATED APPLICATIONS

This application claims priority from U.S. Provisional Application No. 60/380,227, filed May 13, 2002, and U.S. Provisional Application No. 60/463,419, filed Apr. 16, 2003, the contents of which are incorporated herein by reference.

BACKGROUND

Low-density lipoprotein (LDL) receptors (LDLRs) are cell surface receptors involved in general intracellular membrane cycling and endocytosis. The functions of LDLRs include (1) cargo transport for internalizing extracellular components into the endosomal compartment, and (2) lipoproteins metabolism for maintaining cholesterol homeostasis in the body.

LDLRs are members of a receptor superfamily, which also includes LDL receptor-related proteins (LRPs). The roles of LRPs are more restricted than that of LDLRs in lipid metabolism. However, in addition to cargo transport and lipid metabolism, the LRPs are also involved in other cellular processes such as signal transduction that significantly impacts cell metabolism and physiology.

Several LRPs have been identified, including LRP-1, LRP-1b, LRP-2, LRP-5, LRP-6, LRP-7, LRP-8, LRP-9, LRP-10, and LRP-11 (Strickland et al. (2002) Trends in Endocrinology and Metabolism 13(2): 66–74; Herz and Strickland (2001) The Journal of Clinical Investigation 108(6): 779–784; and Herz (2001) Neuron 29: 571–581). All LRPs, like LDLRs, contain trans-membrane sequences and are multi-functional proteins. LRPs differ from each other in minor ways, and have similar structural motifs, including, for example, EGF-like repeats, YWTD repeats, O-linked sugar domains, complement-like repeats, and a cytoplasmic domain. LRPs bind to many intracellular and extracellular molecules. Such intracellular molecules include adaptor and scaffold proteins (e.g., Dab-1, FE65, and PSD-95) and such extracellular molecules include lipoproteins, proteinases, bacterial toxins, antibiotics, viruses and proteinase inhibitor complexes.

Lactoferrin, an 80 kDa glycoprotein present in milk and epithelial secretions, is released by inflammatory cells during immune responses. It circulates at a concentration of 2–7 μg/ml in plasma, and is believed to be involved in regulation of iron metabolism, immunity, and embryonic development.

SUMMARY

The present invention is based on the discovery that LRP-1 and LRP-2 genes are expressed in bone cells.

One aspect of the invention features a method of diagnosing a bone condition.

In one example, the method inludes providing a test sample (e.g., a bone tissue) from a patient suspected of suffering from or being at risk for developing a bone condition, and quantifying the expression level of an LRP-1 gene. The expression level of the LRP-1 gene in the test sample, if different from that in a normal sample, indicates that the patient is suffering from or at risk for developing a bone condition.

In another example, the method inludes providing a test sample from a bone tissue of a patient suspected of suffering from or being at risk for developing a bone condition, and quantifying the expression level of an LRP-2 gene. The expression level of the LRP-2 gene in the test sample, if different from that in a normal sample, indicates that the patient is suffering from or at risk for developing a bone condition.

In another example, the method inludes providing a test sample (e.g., a bone tissue) from a patient suspected of suffering from or being at risk for developing a bone condition, and quantifying the activity of an LRP-1 protein. The activity of the LRP-1 protein in the test sample, if different from that in a normal sample, indicates that the patient is suffering from or at risk for developing a bone condition.

In still another example, the method inludes providing a test sample from a bone tissue of a patient suspected of suffering from or being at risk for developing a bone condition, and quantifying the activity of an LRP-2 protein. The activity of the LRP-2 protein in the test sample, if different from that in a normal sample, indicates that the patient is suffering from or at risk for developing a bone condition.

Another aspect of the invention features a method of identifying a candidate compound for treating a bone condition.

In one example, the method includes contacting a compound with a cell, for example, a bone cell (e.g., an osteoblast cell, osteoblast-like cell such as SaOS-2 cell, osteocyte, or osteoclast cell) expressing an LRP-1 gene, and quantifying the expression level of the LRP-1 gene in the cell. The expression level of the LRP-1 gene in the presence of the compound, if different from that in the absence of the compound, indicates that the compound is a candidate for treating a bone condition.

In another example, the method includes contacting a compound with a bone cell (e.g., an osteoblast cell, osteoblast-like cell such as SaOS-2 cell, osteocyte, or osteoclast cell) expressing an LRP-2 gene, and quantifying the expression level of the LRP-2 gene in the cell. The expression level of the LRP-2 gene in the presence of the compound, if different from that in the absence of the compound, indicates that the compound is a candidate for treating a bone condition.

In another example, the method includes contacting a compound with a cell expressing an LRP-1 gene encoding an LRP-1 protein, and quantifying the activity of the LRP-1 protein in the cell. The activity of the LRP-1 protein in the presence of the compound, if different from that in the absence of the compound, indicates that the compound is a candidate for treating a bone condition.

In still another example, the method includes contacting a compound with a bone cell expressing an LRP-2 gene encoding an LRP-2 protein, and quantifying the activity of the LRP-2 protein in the cell. The activity of the LRP-2 protein in the presence of the compound, if different from that in the absence of the compound, indicates that the compound is a candidate for treating a bone condition.

Also within the scope of the invention is a method of treating a bone condition by modulating the level or activity of an LRP-1 or LRP-2 protein in bone cells.

In one example, the method includes administering to a subject in need thereof an effective amount of a pharmaceutical composition, thereby modulating a level of an LRP-1 or LRP-2 protein in bone cells. The level of the LRP-1 or LRP-2 protein can be modulated by providing and expressing a nucleic acid encoding an LRP-1 or LRP-2 protein, by providing an LRP-1 or LRP-2 protein, or by providing and expressing a nucleic acid complementary to a sequence encoding an LRP-1 or LRP-2 protein, i.e., an anti-sense molecule.

In another example, the method includes administering to a subject in need thereof an effective amount of a pharmaceutical composition, thereby modulating the activity of an LRP-1 or LRP-2 protein in bone cells. The activity of the LRP-1 or LRP-2 protein can be modulated by providing an agonist of the LRP-1 or LRP-2 protein, by providing an antagonist of the LRP-1 or LRP-2 protein, or by providing an antibody against the LRP-1 or LRP-2 protein.

The pharmaceutical composition can be directly administered into the bone cells. It can also be administered to a subject without being directly introduced into bone cells in order to modulate the activity of LRP-1 in the bone cells.

Methods of diagnosing a bone condition, identifying a candidate compound for treating a bone condition, and treating a bone condition involving both LRP-1 and LRP-2 are within the scope of this invention.

The naturally occurring LRP-1 or LRP-2 protein, fragments thereof, biologically active portion thereof, and derivatives thereof are collectively referred to as "LRP-1 or LRP-2 polypeptides or proteins". Nucleic acid molecules encoding such polypeptides or proteins are collectively referred to as "LRP-1 or LRP-2 nucleic acids" (e.g., naturally occurring genes or recombinant genes). LRP-1 or LRP-2 molecules refer to LRP-1 or LRP-2 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded.

As used herein, the terms "gene" and "recombinant gene" refer to nucleic acid molecules which include at least an open reading frame encoding an LRP-1 or LRP-2 protein. The gene can optionally further include non-coding sequences, e.g., regulatory sequences and introns.

As used herein, a "biologically active portion" of an LRP-1 or LRP-2 protein includes a fragment of an LRP-1 or LRP-2 protein which participates in an interaction, e.g., an intramolecular or an intermolecular interaction. An intermolecular interaction can be a specific binding interaction or an enzymatic interaction (e.g., the interaction can be transient and one in which a covalent bond is formed or broken). An intermolecular interaction can be between an LRP-1 or LRP-2 molecule and a non-LRP-1 or LRP-2 molecule or between a first LRP-1 or LRP-2 molecule and a second LRP-1 or LRP-2 molecule. Biologically active portions of an LRP-1 or LRP-2 protein include peptides comprising amino acid sequences sufficiently homologous to or derived from the amino acid sequence of the LRP-1 or LRP-2 protein, which include less amino acids than the full length LRP-1 or LRP-2 proteins, and exhibit at least one activity of an LRP-1 or LRP-2 protein. Typically, biologically active portions contain a domain or motif with at least one activity of the LRP-1 or LRP-2 protein, e.g., cargo transport, lipid metabolism, and signal transduction. A biologically active portion of an LRP-1 or LRP-2 protein can be a polypeptide which is, for example, 10, 25, 50, 100, 200 or more amino acids in length. Biologically active portions of an LRP-1 or LRP-2 protein can be used as targets for developing agents which modulate an LRP-1 or LRP-2-mediated activity, e.g., cargo transport, lipid metabolism, and signal transduction.

As used herein, an "LRP-1 or LRP-2 activity," "biological activity of LRP-1 or LRP-2," or "functional activity of LRP-1 or LRP-2," refers to an activity exerted by an LRP-1 or LRP-2 polypeptide, protein, or nucleic acid molecule. For example, an LRP-1 or LRP-2 activity can be an activity exerted by LRP-1 or LRP-2 in a physiological milieu on, e.g., an LRP-1 or LRP-2-responsive cell or on an LRP-1 or LRP-2 substrate such as a protein substrate. An LRP-1 or LRP-2 activity can be determined in vivo or in vitro. In one example, an LRP-1 or LRP-2 activity is a direct activity, such as an association with an LRP-1 or LRP-2 target molecule. A "target molecule" or "binding partner" is a molecule with which an LRP-1 or LRP-2 protein binds or interacts in nature.

An LRP-1 or LRP-2 activity can also be an indirect activity, e.g., a cellular signaling activity mediated by interaction of the LRP-1 or LRP-2 protein with an LRP-1 or LRP-2 ligand.

Aberrant expression or activity of LRP-1 or LRP-2 or both molecules can mediate disorders associated with bone metabolism. "Bone metabolism" refers to direct or indirect effects in the formation or degeneration of bone structures, e.g., bone formation, bone resorption, and the balance between the two metabolic processes. This term also includes activities mediated by LRP-1 or LRP-2 molecules in bone cells, e.g., osteoclasts and osteoblasts, that in turn result in bone formation and degeneration. For example, LRP-1 or LRP-2 molecules can support different activities of bone resorbing osteoclasts such as the stimulation of differentiation of monocytes and mononuclear phagocytes into osteoclasts. Accordingly, LRP-1 or LRP-2 molecules that modulate the production of bone cells can influence bone formation and degeneration, and thus be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia, milk fever, Paget's disease, and osteogenesis imperfecta.

"Misexpression or aberrant expression", as used herein, refers to a non-wild type pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

As used herein, a "compound" includes, e.g., nucleic acids, proteins, peptides, peptidomimetics, peptoids, or small molecules. An "agonist" refers to a compound that enhances the activity of the LRP-1 or LRP-2 protein; it can be a naturally occurring ligand for LRP-1 or LRP-2. An "antagonist" refers to a compound that inhibits the activity of the LRP-1 or LRP-2 protein.

As used herein, a "subject" refers to a human or a non-human animal.

This invention also relates to diagnosing and treating bone or cartilage conditions by determining and modulating interaction between lactoferrin and a low-density lipoprotein receptor-related protein (LRP-1 or LRP-2) or MAP kinase in bone or cartilage cells.

In one aspect, the invention features a method of determining whether a subject is suffering from or at risk for developing a bone or cartilage condition. The method involves providing a test sample (e.g., a bone or cartilage tissue sample) from a subject, and determining the level of interaction between a lactoferrin polypeptide and an LRP-1 protein, an LRP-2 protein, or a p42/44 MAP kinase in the test sample. If the level of such interaction in the test sample is different from that in a normal sample, it indicates that the subject is suffering from or at risk for developing a bone or cartilage condition. Interaction between lactoferrin and LRP-1, LRP-2, or p42/44 MAP kinase can be determined, e.g., by measuring binding of lactoferrin to LRP-1 or LRP-2, endocytosis of lactoferrin mediated by LRP-1 or LRP-2, or phosphorylation of p42/44 MAP kinase.

In another aspect, the invention features a method of identifying a candidate compound for treating a bone or cartilage condition. The method involves introducing a compound to a system containing a lactoferrin polypeptide and an LRP-1 protein, an LRP-2 protein, or a p42/44 MAP kinase, and determining the level of interaction between the lactoferrin polypeptide and the LRP-1 protein, the LRP-2 protein, or the p42/44 MAP kinase. The system can be a cell system, e.g., containing osteoblastic, osteoclastic or fibroblastic cells or chondrocytes, or a cell-free system. If the level of the interaction between lactoferrin and LRP-1, LRP-2, or p42/44 MAP kinase in the presence of the compound is different from that in the absence of the compound, it indicates that the compound is a candidate for treating a bone or cartilage condition.

In still another aspect, the invention features a method of treating a bone or cartilage condition by modulating interaction between a lactoferrin polypeptide and an LRP-1 protein, an LRP-2 protein, or a p42/44 MAP kinase in bone or cartilage cells. In one example, the interaction is modulated by providing an agonist of LRP-1, LRP-2, or p42/44 MAP kinase, e.g., an exogenous lactoferrin polypeptide. In another example, the interaction is modulated by providing an antagonist of LRP-1 or LRP-2 (e.g., a receptor-associated protein), or an antagonist of p42/44 MAP kinase (e.g., a p42/44 MAP kinase inhibitor, i.e., a compound that inhibits expression, phosphorylation, or activity of a p42/44 MAP kinase such as PD98059 and U-0126). The agonist or antagonist of LRP-1, LRP-2, or p42/44 MAP kinase can be introduced directly into bone or cartilage cells. These agonists or antagonists can be used individually or in combination, sequentially or concurrently, with or without other bone- or cartilage-healing therapies.

A "lactoferrin polypeptide" can be a naturally occurring polypeptide, a recombinant polypeptide, or a synthetic polypeptide. Variants of a wild-type lactoferrin polypeptide (e.g., a fragment of the wild-type lactoferrin polypeptide containing at least 2 (e.g., 4, 6, 8, 10, 20, 50, 100, 200, 300, 400, 500, 600, 700) amino acids, or a recombinant protein containing a lactoferrin polypeptide sequence that maintain the biological activity of a wild-type lactoferrin polypeptide) are within the scope of the invention. The lactoferrin polypeptide can be of a mammalian origin, e.g., from human or bovine milk. The metal ion bound to the polypeptide can be an iron ion (as in a naturally occurring lactoferrin polypeptide), a copper ion, a chromium ion, a cobalt ion, a manganese ion, a zinc ion, or a magnesium ion, or any other co-ordinating metal ion such as scandium or bismuth.

The details of one or more embodiments of the invention are set forth in the accompanying description below. Other features, objects, and advantages of the invention will be apparent from the detailed description, and from the claims.

DETAILED DESCRIPTION

The LRP-1 and LRP-2 nucleic acid molecules, proteins, protein homologues, agonists, antagonists and antibodies can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The LRP-1 and LRP-2 nucleic acid molecules can be used, for example, to express an LRP-1 or LRP-2 protein (e.g., via a recombinant expression vector in a host cell in gene therapy applications), to detect an LRP-1 or LRP-2 mRNA (e.g., in a biological sample) or a genetic alteration in an LRP-1 or LRP-2 gene, and to modulate LRP-1 or LRP-2 activity, as described further below. The LRP-1 or LRP-2 proteins can be used to treat disorders characterized by insufficient or excessive production of an LRP-1 or LRP-2 substrate or production of LRP-1 or LRP-2 inhibitors. In addition, the LRP-1 or LRP-2 proteins can be used to screen for naturally occurring LRP-1 or LRP-2 substrates, to screen for drugs or compounds which modulate LRP-1 or LRP-2 activity, as well as to treat disorders characterized by insufficient or excessive production of LRP-1 or LRP-2 protein or production of LRP-1 or LRP-2 protein forms which have decreased, aberrant or unwanted activity compared to LRP-1 or LRP-2 wild type protein (e.g., bone disorders such as osteoporosis, Paget's disease, and osteogenesis imperfecta). Moreover, the anti-LRP-1 or LRP-2 antibodies can be used to detect and isolate LRP-1 or LRP-2 proteins, regulate the bioavailability of LRP-1 or LRP-2 proteins, and modulate LRP-1 or LRP-2 activity.

A method of evaluating a compound for the ability to interact with, e.g., bind, a subject LRP-1 or LRP-2 polypeptide is provided. The method includes: contacting the compound with the subject LRP-1 or LRP-2 polypeptide; and evaluating ability of the compound to interact with, e.g., to bind or form a complex with the subject LRP-1 or LRP-2 polypeptide. This method can be performed in vitro, e.g., in a cell free system, or in vivo, e.g., in a two-hybrid interaction trap assay. This method can be used to identify naturally occurring molecules that interact with subject LRP-1 or LRP-2 polypeptide. It can also be used to find natural or synthetic inhibitors of subject LRP-1 or LRP-2 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to LRP-1 or LRP-2 proteins, have a stimulatory or inhibitory effect on, for example, LRP-1 or LRP-2 expression or LRP-1 or LRP-2 activity, or have a stimulatory or inhibitory effect on, for example, the expression or activity of an LRP-1 or LRP-2 substrate. Compounds thus identified can be used to modulate the activity of target gene products (e.g., LRP-1 or LRP-2 genes) in a therapeutic protocol, to elaborate the biological function of the target gene product, or to identify compounds that disrupt normal target gene interactions.

In one embodiment, the invention provides assays for screening candidate or test compounds which are substrates of an LRP-1 or LRP-2 protein or polypeptide or a biologically active portion thereof. In another embodiment, the invention provides assays for screening candidate or test compounds that bind to or modulate an activity of an LRP-1 or LRP-2 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses an LRP-1 or LRP-2 protein or biologically active portion thereof is contacted with a test compound, and the ability of the test compound to modulate LRP-1 or LRP-2 activity is determined. Determining the ability of the test compound to modulate LRP-1 or LRP-2 activity can be accomplished by monitoring, for example, cargo transport, lipid metabolism, signal transduction or some other aspect of cell activity, e.g., cell proliferation, mineral deposition or dissolution, or protein synthesis. The cell, for example, can be of mammalian origin, e.g., human.

The ability of the test compound to modulate LRP-1 or LRP-2 binding to a compound, e.g., an LRP-1 or LRP-2 substrate, or to bind to LRP-1 or LRP-2 can also be evaluated. This can be accomplished, for example, by coupling the compound, e.g., the substrate, with a radioisotope or enzymatic label such that binding of the compound, e.g., the substrate, to LRP-1 or LRP-2 can be determined by detecting the labeled compound, e.g., substrate, in a complex. Alternatively, LRP-1 or LRP-2 could be coupled with a radioisotope or enzymatic label to monitor the ability of a test compound to modulate LRP-1 or LRP-2 binding to an LRP-1 or LRP-2 substrate in a complex. For example, compounds (e.g., LRP-1 or LRP-2 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an LRP-1 or LRP-2 substrate) to interact with LRP-1 or LRP-2 with or without the labeling of any of the interactants can be evaluated. For example, a microphysiometer can be used to detect the interaction of a compound with LRP-1 or LRP-2 without the labeling of either the compound or the LRP-1 or LRP-2 (McConnell, H. M. et al. (1992) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and LRP-1 or LRP-2.

In yet another embodiment, a cell-free assay is provided in which an LRP-1 or LRP-2 protein or biologically active portion thereof is contacted with a test compound and the ability of the test compound to bind to the LRP-1 or LRP-2 protein or biologically active portion thereof is evaluated. Preferred biologically active portions of the LRP-1 or LRP-2 proteins to be used in assays of the present invention include fragments which participate in interactions with non-LRP-1 or LRP-2 molecules, e.g., fragments with high surface probability scores.

Soluble or membrane-bound forms of isolated proteins (e.g., LRP-1 or LRP-2 proteins or biologically active portions thereof) can be used in the cell-free assays of the invention. When membrane-bound forms of the protein are used, it is desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the LRP-1 or LRP-2 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It is desirable to immobilize either LRP-1 or LRP-2, an anti-LRP-1 or LRP-2 antibody or its target molecule to facilitate separation of complexed from uncomplexed forms of one or both of the proteins, as well as to accommodate automation of the assay. Binding of a test compound to an LRP-1 or LRP-2 protein, or interaction of an LRP-1 or LRP-2 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/LRP-1 or LRP-2 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or LRP-1 or LRP-2 protein, and the mixture incubated under conditions conducive to complex formation (e.g., at physiological conditions for salt and pH). Following incubation, the beads or microtiter plate wells are washed to remove any unbound components, the matrix immobilized in the case of beads, the complex so formed determined either directly or indirectly, for example, as described above. Alternatively, the complexes can be dissociated from the matrix, and the level of LRP-1 or LRP-2 binding or activity determined using standard techniques.

Other techniques for immobilizing either an LRP-1 or LRP-2 protein or a target molecule on matrices include using conjugation of biotin and streptavidin. Biotinylated LRP-1 or LRP-2 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with LRP-1 or LRP-2 protein or target molecules but which do not interfere with binding of the LRP-1 or LRP-2 protein to its target molecule. Such antibodies can be derivatized to the wells of the plate, and unbound target or LRP-1 or LRP-2 protein trapped in the wells by antibody conjugation. Methods for detecting such complexes, in addition to those described above for the GST-immobilized complexes, include immunodetection of complexes using antibodies reactive with the LRP-1 or LRP-2 protein or target molecule, as well as enzyme-linked assays which rely on detecting an enzymatic activity associated with the LRP-1 or LRP-2 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141–8; Hage, D. S., and Tweed, S. A. (1997) *J Chromatogr B Biomed Sci Appl.* 699:499–525). Further, fluorescence energy transfer can also be conveniently utilized, as described herein, to detect binding without further purification of the complex from solution.

In a preferred embodiment, the assay includes contacting the LRP-1 or LRP-2 protein or biologically active portion thereof with a known compound which binds LRP-1 or LRP-2 to form an assay mixture, contacting the assay mixture with a test compound, and determining the ability of the test compound to interact with an LRP-1 or LRP-2 protein, wherein determining the ability of the test compound to interact with an LRP-1 or LRP-2 protein includes determining the ability of the test compound to preferentially bind to LRP-1 or LRP-2 or biologically active portion thereof, or to modulate the activity of a target molecule, as compared to the known compound.

The target gene products can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the LRP-1 or LRP-2 genes herein identified. In an alternative embodiment, the invention provides methods for determining the ability of the test compound to modulate the activity of an LRP-1 or LRP-2 protein through modulation of the activity of a downstream effector of an LRP-1 or LRP-2 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the LRP-1 or LRP-2 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with LRP-1 or LRP-2 ("LRP-1 or LRP-2-binding proteins" or "LRP-1 or LRP-2-bp") and are involved in LRP-1 or LRP-2 activity. Such LRP-1 or LRP-2-bps can be activators or inhibitors of signals by the LRP-1 or LRP-2 proteins or LRP-1 or LRP-2 targets as, for example, downstream elements of an LRP-1 or LRP-2-mediated signaling pathway.

The two-hybrid system is based on the modular nature of most transcription factors, which consist of separable DNA-binding and activation domains. Briefly, the assay utilizes two different DNA constructs. In one construct, the gene that codes for an LRP-1 or LRP-2 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: LRP-1 or LRP-2 protein can be the fused to the activator domain.) If the "bait" and the "prey" proteins are able to interact, in vivo, forming an LRP-1 or LRP-2-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the LRP-1 or LRP-2 protein.

In another embodiment, modulators of LRP-1 or LRP-2 expression are identified. For example, a cell or cell free mixture is contacted with a candidate compound and the expression of LRP-1 or LRP-2 mRNA or protein evaluated relative to the level of expression of LRP-1 or LRP-2 mRNA or protein in the absence of the candidate compound. When expression of LRP-1 or LRP-2 mRNA or protein is greater in the presence of the candidate compound than in its absence, the candidate compound is identified as a stimulator of LRP-1 or LRP-2 mRNA or protein expression. Alternatively, when expression of LRP-1 or LRP-2 mRNA or protein is less (statistically significantly less) in the presence of the candidate compound than in its absence, the candidate compound is identified as an inhibitor of LRP-1 or LRP-2 mRNA or protein expression. The level of LRP-1 or LRP-2 mRNA or protein expression can be determined by methods described herein for detecting LRP-1 or LRP-2 mRNA or protein.

In another aspect, the invention pertains to a combination of two or more of the assays described herein. For example, a modulating agent can be identified using a cell-based or a cell free assay, and the ability of the agent to modulate the activity of an LRP-1 or LRP-2 protein can be confirmed in vivo, e.g., in an animal such as an animal model for bone disorders such as osteoporosis, Paget's disease, and osteogenesis imperfecta.

This invention further pertains to novel agents identified by the above-described screening assays. Accordingly, it is within the scope of this invention to further use an agent identified as described herein (e.g., an LRP-1 or LRP-2 modulating agent, an antisense LRP-1 or LRP-2 nucleic acid molecule, an LRP-1 or LRP-2-specific antibody, or an LRP-1 or LRP-2-binding partner) in an appropriate animal model to determine the efficacy, toxicity, side effects, or mechanism of action, of treatment with such an agent. Furthermore, novel agents identified by the above-described screening assays can be used for treatments as described herein.

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes LRP-1 or LRP-2.

Such disorders include, e.g., a disorder associated with the misexpression of LRP-1 or LRP-2 gene; a disorder of bone.

The method includes one or more of the following:

detecting, in a tissue of the subject, the presence or absence of a mutation which affects the expression of the LRP-1 or LRP-2 gene, or detecting the presence or absence of a mutation in a region which controls the expression of the gene, e.g., a mutation in the 5' control region;

detecting, in a tissue of the subject, the presence or absence of a mutation which alters the structure of the LRP-1 or LRP-2 gene;

detecting, in a tissue of the subject, the misexpression of the LRP-1 or LRP-2 gene, at the mRNA level, e.g., detecting a non-wild type level of a mRNA;

detecting, in a tissue of the subject, the misexpression of the gene, at the protein level, e.g., detecting a non-wild type level of an LRP-1 or LRP-2 polypeptide.

In preferred embodiments the method includes: ascertaining the existence of at least one of: a deletion of one or more nucleotides from the LRP-1 or LRP-2 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from naturally occurring mutants thereof or 5' or 3' flanking sequences naturally associated with the LRP-1 or LRP-2 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the LRP-1 or LRP-2 gene; the presence of a non-wild type splicing pattern of a messenger RNA transcript of the gene; or a non-wild type level of LRP-1 or LRP-2.

Methods of the invention can be used prenatally or to determine if a subject's offspring will be at risk for a disorder.

In preferred embodiments the method includes determining the structure of an LRP-1 or LRP-2 gene, an abnormal structure being indicative of risk for the disorder.

In preferred embodiments the method includes contacting a sample from the subject with an antibody to the LRP-1 or LRP-2 protein or a nucleic acid, which hybridizes specifically with the gene. These and other embodiments are discussed below.

Diagnostic and Prognostic Assays

Diagnostic and prognostic assays of the invention include method for assessing the expression level of LRP-1 or LRP-2 molecules and for identifying variations and mutations in the sequence of LRP-1 or LRP-2 molecules.

Expression Monitoring and Profiling

The presence, level, or absence of LRP-1 or LRP-2 protein or nucleic acid in a biological sample can be evaluated by obtaining a biological sample from a test subject and contacting the biological sample with a compound or an agent capable of detecting LRP-1 or LRP-2 protein or nucleic acid (e.g., mRNA, genomic DNA) that encodes LRP-1 or LRP-2 protein such that the presence of LRP-1 or LRP-2 protein or nucleic acid is detected in the biological sample. The term "biological sample" includes tissues, cells and biological fluids isolated from a subject, as well as tissues, cells and fluids present within a subject. A preferred biological sample is serum. The level of expression of the LRP-1 or LRP-2 gene can be measured in a number of ways, including, but not limited to: measuring the mRNA encoded by the LRP-1 or LRP-2 genes; measuring the amount of protein encoded by the LRP-1 or LRP-2 genes; or measuring the activity of the protein encoded by the LRP-1 or LRP-2 genes.

The level of mRNA corresponding to the LRP-1 or LRP-2 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length LRP-1 or LRP-2 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to LRP-1 or LRP-2 mRNA or genomic DNA. The probe can be disposed on an address of an alTay, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the LRP-1 or LRP-2 genes.

The level of mRNA in a sample that is encoded by one of LRP-1 or LRP-2 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the LRP-1 or LRP-2 gene being analyzed.

In another embodiment, the methods further contacting a control sample with a compound or agent capable of detecting LRP-1 or LRP-2 mRNA, or genomic DNA, and comparing the presence of LRP-1 or LRP-2 mRNA or genomic DNA in the control sample with the presence of LRP-1 or LRP-2 mRNA or genomic DNA in the test sample. In still another embodiment, serial analysis of gene expression, as described in U.S. Pat. No. 5,695,937, is used to detect LRP-1 or LRP-2 transcript levels.

A variety of methods can be used to determine the level of protein encoded by LRP-1 or LRP-2. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect LRP-1 or LRP-2 protein in a biological sample in vitro as well as in vivo. In vitro techniques for detection of LRP-1 or LRP-2 protein include enzyme linked immunosorbent assays (ELISAs), immunoprecipitations, immunofluorescence, enzyme immunoassay (EIA), radioimmunoassay (RIA), and Western blot analysis. In vivo techniques for detection of LRP-1 or LRP-2 protein include introducing into a subject a labeled anti-LRP-1 or LRP-2 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-LRP-1 or LRP-2 antibody positioned on an antibody array (as described below). The sample can be detected, e.g., with avidin coupled to a fluorescent label.

In another embodiment, the methods further include contacting the control sample with a compound or agent capable of detecting LRP-1 or LRP-2 protein, and comparing the presence of LRP-1 or LRP-2 protein in the control sample with the presence of LRP-1 or LRP-2 protein in the test sample.

The invention also includes kits for detecting the presence of LRP-1 or LRP-2 in a biological sample. For example, the kit can include a compound or agent capable of detecting LRP-1 or LRP-2 protein or mRNA in a biological sample; and a standard. The compound or agent can be packaged in a suitable container. The kit can further comprise instructions for using the kit to detect LRP-1 or LRP-2 protein or nucleic acid or an agonist or antagonist of the LRP-1 or LRP-2 protein.

For antibody-based kits, the kit can include: (1) a first antibody (e.g., attached to a solid support) which binds to a polypeptide corresponding to a marker; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker or (2) a pair of primers useful for amplifying a nucleic acid molecule corresponding to a marker. The kit can also include a buffering agent, a preservative, or a protein stabilizing agent. The kit can also include components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted LRP-1 or LRP-2 expression or activity. As used herein, the term "unwanted" includes an unwanted phenomenon involved in a biological response such as bone disorders such as osteoporosis, Paget's disease, and osteogenesis imperfecta.

In one embodiment, a disease or disorder associated with aberrant or unwanted LRP-1 or LRP-2 expression or activity is identified. A test sample is obtained from a subject and LRP-1 or LRP-2 protein or nucleic acid (e.g., mRNA or genomic DNA) is evaluated, wherein the level, e.g., the presence or absence, of LRP-1 or LRP-2 protein or nucleic acid is diagnostic for a subject having or at risk of developing a disease or disorder associated with aberrant or unwanted LRP-1 or LRP-2 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted LRP-1 or LRP-2 expression or activity. For example, such methods can be used to determine whether a subject can be effectively treated with an agent for a bone disorder such as osteoporosis, Paget's disease, or osteogenesis imperfecta.

In another aspect, the invention features a computer medium having a plurality of digitally encoded data records. Each data record includes a value representing the level of expression of LRP-1 or LRP-2 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than LRP-1 or LRP-2 (e.g., other genes associated with an LRP-1 or LRP-2-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of LRP-1 or LRP-2 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a bone disorders such as osteoporosis, Paget's disease, and osteogenesis imperfecta in a subject wherein an increase/decrease in LRP-1 or LRP-2 expression is an indication that the subject has or is disposed to having a bone disorders such as osteoporosis, Paget's disease, and osteogenesis imperfecta. The method can be used to monitor a treatment for bone disorders such as osteoporosis, Paget's disease, and osteogenesis imperfecta in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of LRP-1 or LRP-2 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of LRP-1 or LRP-2 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of LRP-1 or LRP-2 expression.

Detection of Variations or Mutations

The methods of the invention can also be used to detect genetic alterations in an LRP-1 or LRP-2 gene, thereby determining if a subject with the altered gene is at risk for a disorder characterized by misregulation in LRP-1 or LRP-2 protein activity or nucleic acid expression, such as a bone disorder (e.g., osteoporosis, Paget's disease, or osteogenesis imperfecta). In preferred embodiments, the methods include detecting, in a sample from the subject, the presence or absence of a genetic alteration characterized by at least one of an alteration affecting the integrity of a gene encoding an LRP-1 or LRP-2-protein, or the misexpression of the LRP-1 or LRP-2 gene. For example, such genetic alterations can be detected by ascertaining the existence of at least one of 1) a deletion of one or more nucleotides from an LRP-1 or LRP-2 gene; 2) an addition of one or more nucleotides to an LRP-1 or LRP-2 gene; 3) a substitution of one or more nucleotides of an LRP-1 or LRP-2 gene, 4) a chromosomal rearrangement of an LRP-1 or LRP-2 gene; 5) an alteration in the level of a messenger RNA transcript of an LRP-1 or LRP-2 gene, 6) aberrant modification of an LRP-1 or LRP-2 gene, such as of the methylation pattern of the genomic DNA, 7) the presence of a non-wild type splicing pattern of a messenger RNA transcript of an LRP-1 or LRP-2 gene, 8) a non-wild type level of an LRP-1 or LRP-2-protein, 9) allelic loss of an LRP-1 or LRP-2 gene, and 10) inappropriate post-translational modification of an LRP-1 or LRP-2-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the LRP-1 or LRP-2-gene. This method can include the steps of collecting a sample of cells from a subject, isolating nucleic acid (e.g., genomic, mRNA or both) from the sample, contacting the nucleic acid sample with one or more primers which specifically hybridize to an LRP-1 or LRP-2 gene under conditions such that hybridization and amplification of the LRP-1 or LRP-2-gene (if present) occurs, and detecting the presence or absence of an amplification product, or detecting the size of the amplification product and comparing the length to a control sample. It is anticipated that PCR or LCR can be desirable to use as a preliminary amplification step in conjunction with any of the techniques used for detecting mutations described herein. Alternatively, other amplification methods described herein or known in the art can be used.

In another embodiment, mutations in an LRP-1 or LRP-2 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in LRP-1 or LRP-2 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of an LRP-1 or LRP-2 nucleic acid or a putative variant (e.g., allelic variant) thereof. A probe can have one or more mismatches to a region of an LRP-1 or LRP-2 nucleic acid (e.g., a destabilizing mismatch). The arrays can have a high density of addresses, e.g., can contain hundreds or thousands of oligonucleotides probes (Cronin, M. T. et al. (1996) Human Mutation 7: 244–255; Kozal, M. J. et al. (1996) Nature Medicine 2: 753–759). For example, genetic mutations in LRP-1 or LRP-2 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the LRP-1 or LRP-2 gene and detect mutations by comparing the sequence of the sample LRP-1 or LRP-2 with the corresponding wild-type (control) sequence. Automated sequencing procedures can be utilized when performing the diagnostic assays ((1995) Biotechniques 19:448), including sequencing by mass spectrometry.

Other methods for detecting mutations in the LRP-1 or LRP-2 gene include methods in which protection from cleavage agents is used to detect mismatched bases in RNA/RNA or RNA/DNA heteroduplexes (Myers et al. (1985) Science 230:1242; Cotton et al. (1988) Proc. Natl Acad Sci USA 85:4397; Saleeba et al. (1992) Methods Enzymol. 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in LRP-1 or LRP-2 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662; U.S. Pat. No. 5,459,039).

In other embodiments, alterations in electrophoretic mobility will be used to identify mutations in LRP-1 or LRP-2 genes. For example, single strand conformation polymorphism (SSCP) can be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet. Anal. Tech. Appl. 9:73–79). Single-stranded DNA fragments of sample and control LRP-1 or LRP-2 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it is desirable to introduce a novel restriction site in the region of the mutation to create cleavage-based detection (Gasparini et al. (1992) *Mol. Cell Probes* 6:1). It is anticipated that in certain embodiments amplification can also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to an LRP-1 or LRP-2 nucleic acid.

In a preferred embodiment the set includes a first and a second oligonucleotide. The first and second oligonucleotide can hybridize to the same or to different locations of an LRP-1 or LRP-2 gene sequence or the complement of an LRP-1 or LRP-2 gene sequence. Different locations can be different but overlapping, or non-overlapping on the same strand. The first and second oligonucleotide can hybridize to sites on the same or on different strands.

The set can be useful, e.g., for identifying SNP's, or identifying specific alleles of LRP-1 or LRP-2. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, an LRP-1 or LRP-2 nucleic acid.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving an LRP-1 or LRP-2 gene.

Use of LRP-1 or LRP-2 Molecules as Surrogate Markers

The LRP-1 or LRP-2 molecules are also useful as markers of disorders or disease states, as markers for precursors of disease states, as markers for predisposition of disease states, as markers of drug activity, or as markers of the pharmacogenomic profile of a subject. Using the methods described herein, the presence, absence or quantity of the LRP-1 or LRP-2 molecules can be detected, and can be correlated with one or more biological states in vivo. For example, the LRP-1 or LRP-2 molecules can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The LRP-1 or LRP-2 molecules are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., an LRP-1 or LRP-2 marker) transcription or expression, the amplified marker can be in a quantity which is more readily detectable than the drug itself. Also, the marker can be more easily detected due to the nature of the marker itself; for example, using the methods described herein, anti-LRP-1 or LRP-2 antibodies can be employed in an immune-based detection system for an LRP-1 or LRP-2 protein marker, or LRP-1 or LRP-2-specific radiolabeled probes can be used to detect an LRP-1 or LRP-2 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am. J. Health-Syst. Pharm.* 56 Suppl. 3: S16–S20.

The LRP-1 or LRP-2 molecules are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, be selected. For example, based on the presence or quantity of RNA, or protein (e.g., LRP-1 or LRP-2 protein or RNA) for specific tumor markers in a subject, a drug or course of treatment be selected that is optimized for the treatment of the specific tumor likely to be present in the subject. Similarly, the presence or absence of a specific sequence mutation in LRP-1 or LRP-2 DNA correlate LRP-1 or LRP-2 drug response. The use of pharmacogenomic markers therefore permits the application of the most appropriate treatment for each subject without having to administer the therapy.

Methods of Treatment

The present invention provides for both prophylactic and therapeutic methods of treating a subject at risk of (or susceptible to) a disorder or having a disorder associated with aberrant or unwanted LRP-1 or LRP-2 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the LRP-1 or LRP-2 molecules of the present invention or LRP-1 or LRP-2 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted LRP-1 or LRP-2 expression or activity, by administering to the subject an LRP-1 or LRP-2 or an agent which modulates LRP-1 or LRP-2 expression or at least one LRP-1 or LRP-2 activity. Subjects at risk for a disease which is caused or contributed to by aberrant or unwanted LRP-1 or LRP-2 expression or activity can be identified by, for example, any or a combination of diagnostic or prognostic assays as described herein. Administration of a prophylactic agent can occur prior to the manifestation of symptoms characteristic of the LRP-1 or LRP-2 aberrance, such that a disease or disorder is prevented or, alternatively, delayed in its progression. Depending on the type of LRP-1 or LRP-2 aberrance, for example, an LRP-1 or LRP-2, LRP-1 or LRP-2 agonist or LRP-1 or LRP-2 antagonist agent can be used for treating the subject. The appropriate agent can be determined based on screening assays described herein.

It is possible that some LRP-1 or LRP-2-related disorders can be caused, at least in part, by an abnormal level of gene product, or by the presence of a gene product exhibiting abnormal activity. As such, the reduction in the level or activity of such gene products would bring about the amelioration of disorder symptoms.

As discussed, successful treatment of LRP-1 or LRP-2-related disorders can be brought about by techniques that serve to inhibit the expression or activity of target gene products. For example, compounds, e.g., an agent identified using an assays described above, that proves to exhibit negative modulatory activity, can be used in accordance with the invention to prevent or ameliorate symptoms of LRP-1 or LRP-2-related disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, or triple helix molecules to reduce or inhibit mutant gene expression can also reduce or inhibit the transcription (triple helix) or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by LRP-1 or LRP-2 expression is through the use of aptamer molecules specific for LRP-1 or LRP-2 protein. Aptamers are nucleic acid molecules having a tertiary structure which permits them to specifically bind to protein ligands (see, e.g., Osborne, et al. (1997) *Curr. Opin. Chem Biol.* 1: 5–9; and Patel, D. J. (1997) *Curr Opin Chem Biol* 1:32–46). Since nucleic acid molecules can in many cases be more conveniently introduced into target cells than therapeutic protein molecules can be, aptamers offer a method by which LRP-1 or LRP-2 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of LRP-1 or LRP-2-related disorders. For a description of antibodies, see the Antibody section above.

In circumstances wherein injection of an animal or a human subject with an LRP-1 or LRP-2 protein or epitope for stimulating antibody production is harmful to the subject, it is possible to generate an immune response against LRP-1 or LRP-2 through the use of anti-idiotypic antibodies (see, for example, Herlyn, D. (1999) *Ann Med* 31:66–78; and Bhattacharya-Chatterjee, M., and Foon, K. A. (1998) *Cancer Treat Res.* 94:51–68). If an anti-idiotypic antibody is introduced into a mammal or human subject, it should stimulate the production of anti-anti-idiotypic antibodies, which should be specific to the LRP-1 or LRP-2 protein. Vaccines directed to a disease characterized by LRP-1 or LRP-2 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis or activity can be administered to a patient at therapeutically effective doses to prevent, treat or ameliorate LRP-1 or LRP-2-related disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics or "biosensors" that have been created through molecular imprinting techniques. The compound which is able to modulate LRP-1 or LRP-2 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of LRP-1 or LRP-2 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating LRP-1 or LRP-2 expression or activity for therapeutic purposes. Accordingly, in an exemplary embodiment, the modulatory method of the invention involves contacting a cell with an LRP-1 or LRP-2 or agent that modulates one or more of the activities of LRP-1 or LRP-2 protein activity associated with the cell. An agent that modulates LRP-1 or LRP-2 protein activity can be an agent as described herein, such as a nucleic acid or a protein, a naturally-occurring target molecule of an LRP-1 or LRP-2 protein (e.g., an LRP-1 or LRP-2 substrate or receptor), an LRP-1 or LRP-2 antibody, an LRP-1 or LRP-2 agonist or antagonist, a peptidomimetic of an LRP-1 or LRP-2 agonist or antagonist, or other small molecule.

In one embodiment, the agent stimulates one or LRP-1 or LRP-2 activities. Examples of such stimulatory agents include active LRP-1 or LRP-2 protein and a nucleic acid molecule encoding LRP-1 or LRP-2. In another embodiment, the agent inhibits one or more LRP-1 or LRP-2 activities. Examples of such inhibitory agents include antisense LRP-1 or LRP-2 nucleic acid molecules, anti-LRP-1 or LRP-2 antibodies, and LRP-1 or LRP-2 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an LRP-1 or LRP-2 protein or nucleic acid molecule. In one embodiment, the method involves administering an agent (e.g., an agent identified by a screening assay described herein), or combination of agents that modulates (e.g., up regulates or down regulates) LRP-1 or LRP-2 expression or activity. In another embodiment, the method involves administering an LRP-1 or LRP-2 protein or nucleic acid molecule as therapy to compensate for reduced, aberrant, or unwanted LRP-1 or LRP-2 expression or activity.

Stimulation of LRP-1 or LRP-2 activity is desirable in situations in which LRP-1 or LRP-2 is abnormally downregulated or in which increased LRP-1 or LRP-2 activity is likely to have a beneficial effect. For example, stimulation of LRP-1 or LRP-2 activity is desirable in situations in which an LRP-1 or LRP-2 is downregulated or in which increased LRP-1 or LRP-2 activity is likely to have a beneficial effect. Likewise, inhibition of LRP-1 or LRP-2 activity is desirable in situations in which LRP-1 or LRP-2 is abnormally upregulated or in which decreased LRP-1 or LRP-2 activity is likely to have a beneficial effect.

Pharmacogenomics

The LRP-1 or LRP-2 molecules, as well as agents, or modulators which have a stimulatory or inhibitory effect on LRP-1 or LRP-2 activity (e.g., LRP-1 or LRP-2 gene expression) as identified by a screening assay described herein can be administered to individuals to treat (prophylactically or therapeutically) LRP-1 or LRP-2 associated disorders (e.g., bone disorders such as osteoporosis, Paget's disease, and osteogenesis imperfecta) associated with aberrant or unwanted LRP-1 or LRP-2 activity. In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer an LRP-1 or LRP-2 molecule or LRP-1 or LRP-2 modulator as well as tailoring the dosage or therapeutic regimen of treatment with an LRP-1 or LRP-2 molecule or LRP-1 or LRP-2 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority is likely not associated with diseases. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach," can be utilized to identify genes that predict drug response. According to this method, if a gene that encodes a drug's target is known (e.g., an LRP-1 or LRP-2 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., an LRP-1 or LRP-2 molecule or LRP-1 or LRP-2 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with an LRP-1 or LRP-2 molecule or LRP-1 or LRP-2 modulator, such as a modulator identified by one of the exemplary screening assays described herein.

The present invention further provides methods for identifying new agents, or combinations, that are based on identifying agents that modulate the activity of one or more of the gene products encoded by one or more of the LRP-1 or LRP-2 genes of the present invention, wherein these products can be associated with resistance of the cells to a therapeutic agent. Specifically, the activity of the proteins encoded by the LRP-1 or LRP-2 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of an LRP-1 or LRP-2 protein can be applied in clinical trials. For example, the effectiveness of an agent determined by a screening assay as described herein to increase LRP-1 or LRP-2 gene expression, protein levels, or upregulate LRP-1 or LRP-2 activity, can be monitored in clinical trials of subjects exhibiting decreased LRP-1 or LRP-2 gene expression, protein levels, or downregulated LRP-1 or LRP-2 activity. Alternatively, the effectiveness of an agent determined by a screening assay to decrease LRP-1 or LRP-2 gene expression, protein levels, or downregulate LRP-1 or LRP-2 activity, can be monitored in clinical trials of subjects exhibiting increased LRP-1 or LRP-2 gene expression, protein levels, or upregulated LRP-1 or LRP-2 activity. In such clinical trials, the expression or activity of an LRP-1 or LRP-2 gene, and preferably, other genes that have been implicated in, for example, an LRP-1 or LRP-2-associated disorder can be used as a "read out" or markers of the phenotype of a particular cell.

Each of the novel compounds of this invention can be used as a bio-active component for use in bone implants, transplants, prostheses or the like. They can also be used as either neutraceuticals or pharmaceuticals, or both, especially when clinical management of a bone condition requires both nutritional and pharmaceutical intervention.

The methods described above can be used alone or in combination for diagnosing bone diseases, monitoring bone growth and development, or following the course of healing and recovery from bone diseases.

This invention is also based on the unexpected discovery that lactoferrin interacts with LRP-1 and LRP-2 and induces phosphorylation of MAP kinase in bone or cartilage cells. The interaction between lactoferrin and LRP-1, LRP-2, or MAP kinase in bone or cartilage cells can be monitored in diagnosing and treating bone or cartilage conditions, and identifying therapeutic compounds for treating such conditions.

A diagnostic method of the invention involves comparing the level of interaction between a lactoferrin polypeptide and an LRP-1 protein, an LRP-2 protein, or a p42/44 MAP kinase in a sample (e.g., a bone or cartilage tissue sample) prepared from a test subject with that in a sample prepared from a normal subject, i.e., a subject who does not suffer from a bone or cartilage condition. Such interaction can be determined, e.g., by measuring binding of lactoferrin to LRP-1 or LRP-2, endocytosis of lactoferrin mediated by LRP-1 or LRP-2, or phosphorylation of p42/44 MAP kinase, or by any other methods known in the art. A higher or lower level of interaction between lactoferrin and LRP-1, LRP-2, or p42/44 MAP kinase indicates that the test subject is suffering from or at risk for developing a bone or cartilage condition. This method can be used on its own or in conjunction with other procedures to diagnose bone or cartilage conditions.

The invention also provides a method for identifying and manufacturing compounds (e.g., proteins, peptides, peptidomimetics, peptoids, antibodies, or small molecules) that modulate (increase or decrease) interaction between lactoferrin and LRP-1, LRP-2, or p42/44 MAP kinase in a cell (e.g., a bone or cartilage cell). Compounds thus identified can be used, e.g., for preventing and treating bone or cartilage conditions.

The candidate compounds of the present invention can be obtained using any of the numerous approaches described above. To identify compounds that modulate interaction between lactoferrin and LRP-1, LRP-2, or p42/44 MAP kinase, a system (a cell system or a cell-free system) containing lactoferrin and LRP-1, LRP-2, or p42/44 MAP kinase is contacted with a candidate compound and the level of interaction between lactoferrin and LRP-1, LRP-2, or p42/44 MAP kinase is evaluated relative to that in the absence of the candidate compound. In a cell system, e.g., a system containing bone or cartilage cells, the cells can be ones that naturally express lactoferrin and LRP-1, LRP-2, or p42/44 MAP kinase, or ones that are modified to express recombinant lactoferrin and LRP-1, LRP-2, or p42/44 MAP kinase, for example, having lactoferrin and LRP-1, LRP-2, or p42/44 MAP kinase genes fused to marker genes. The level of interaction between lactoferrin and LRP-1, LRP-2, or p42/44 MAP kinase, or the level of interaction between marker proteins, can be determined by methods described above and any other methods known in the art. If the level of interaction between lactoferrin and LRP-1, LRP-2, or p42/44 MAP kinase, or the level of interaction between marker proteins is higher or lower in the presence of the candidate compound than that in the absence of the candidate compound, the candidate compound is identified as being useful for preventing and treating bone or cartilage conditions.

This invention further provides a method for treating a bone or cartilage condition by administering to a subject in need thereof an effective amount of a composition, e.g., containing an agonist or an antagonist of LRP-1, LRP-2, or p42/44 MAP kinase. An "effective amount" is an amount of the composition that is capable of producing a medically desirable result (e.g., an increased or decreased level of interaction between lactoferrin and LRP-1, LRP-2, or p42/44 MAP kinase) in a treated subject. The term "treating" is defined as administration of a composition to a subject, who has a bone or cartilage condition, with the purpose to cure, alleviate, relieve, remedy, prevent, or ameliorate the condition, the symptom of the condition, the disease state secondary to the condition, or the predisposition toward the condition. A subject can be a person who suffers from a bone or cartilage condition, who has positive markers but no clinical evidence of the condition, or who is at risk of the condition for genetic (e.g., familial), habitual (e.g., smoking), or environmental (e.g., radon) reasons. Examples of such bone conditions include, but are not limited to, osteoporosis, rheumatoid, hepatic osteodystrophy, osteomalacia, rickets, osteitis fibrosa cystica, renal osteodystrophy, osteosclerosis, osteopenia, fibrogenesis-imperfecta ossium, secondary hyperparathyrodism, hypoparathyroidism, hyperparathyroidism, chronic renal disease, sarcoidosis, glucocorticoid-induced osteoporosis, idiopathic hypercalcemia, Paget's disease, and osteogenesis imperfecta, bone transplants, non-healing fractures and bone defects. The composition can also be used for stimulating chondrocytes, with the potential of cartilage repair, to treat osteoarthritis and other arthritides and facilitate autologous bone and cartilage transplants in humans, race horses and other animals. Thus, the composition offers the benefit of concurrent healing of bone and cartilage injuries.

Subjects to be treated can be identified, for example, by determining the level of interaction between lactoferrin and LRP-1, LRP-2, or p42/44 MAP kinase in a sample prepared from a subject by methods described above. If the level of such interaction is higher or lower in the sample from the subject than that in a sample from a normal subject, the subject is a candidate for treatment with an effective amount of a compound that decreases or increases the level of interaction between lactoferrin and LRP-1, LRP-2, or p42/

44 MAP kinase in the subject. The treatment method can be performed in vivo or ex vivo, alone or in conjunction with other drugs or therapy.

In one in vivo approach, a therapeutic composition (e.g., a composition containing a compound that modulates interaction between lactoferrin and LRP-1, LRP-2, or p42/44 MAP kinase in a cell) is administered to the subject. Generally, the compound will be suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. For prevention and treatment of bone or cartilage conditions, the compound can be delivered directly to a bone or cartilage lesion or to bone or cartilage cells.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding a lactoferrin polypeptide can be delivered to the subject, for example, by the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) J. Mol. Med. 73, 479). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding a lactoferrin polypeptide is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. As is well known in the medical arts, the dosage will vary. A preferred dosage for administration of polynucleotide is from approximately $10^6$ to $10^{12}$ copies of the polynucleotide molecule. This dose can be repeatedly administered, as needed. Routes of administration can be any of those listed above.

An ex vivo strategy for treating subjects with bone or cartilage conditions can involve transfecting or transducing cells obtained from the subject with a polynucleotide encoding a lactoferrin protein. Alternatively, a cell can be transfected in vitro with a vector designed to insert, by homologous recombination, a new, active promoter upstream of the transcription start site of the naturally occurring endogenous lactoferrin gene in the cell's genome. Such methods, which "switch on" an otherwise largely silent gene, are well known in the art. After selection and expansion of a cell that expresses lactoferrin at a desired level, the transfected or transduced cells are then returned to the subject. The cells can be any of a wide range of types including, without limitation, bone marrow stromal cells, osteoblasts, chondrocytes, or their precursors. Such cells act as a source of lactoferrin for as long as they survive in the subject.

The ex vivo methods include the steps of harvesting cells from a subject, culturing the cells, transducing them with an expression vector, and maintaining the cells under conditions suitable for expression of the lactoferrin gene. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of the lactoferrin gene. The cells may then be injected or implanted into the subject.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Primary Rat Osteoblast-like Cell Culture

Osteoblasts were isolated from 20-day old fetal rat calvariae as previously described (Cornish et al. (1999) Amer. J. Physiol-Endocrinol. Metab. 277:E779–E783). Briefly, calvariae were excised and the frontal and parietal bones, free of suture and periosteal tissue, were collected. After washing, the calvariae were treated twice with 3 mL of 1 mg/mL collagenase for 7 minutes at 37° C. After discarding the supernatants from these two digestions, the calvariae were treated a further twice with 3 mL of 2 mg/mL collagenase (30 mins, 37° C.). The supernatants of the latter two digestions were pooled, centrifuged, and the cells washed. Cells were grown to confluence and then subcultured into 24 well plates. Cells were growth arrested in minimum essential medium (MEM)/0.1% bovine serum albumin for 24 h before harvest.

SaOS-2 Cell Line Culture

The human osteoblast-like osteosarcoma cell line SaOS-2 was maintained in DMEM (GIBCO 12100-046) supplemented with 2.2 g/L $NaHCO_3$, 10% FBS, and 10 ml/L penicillin-streptomycin (GIBCO 15140-122). Cells were plated in 75 $cm^2$ flasks and when confluent used for total RNA isolation or proliferation assays.

Detection of LRP-1 and LRP-2 Gene Expression

LRP-1 and LRP-2 gene expression was identified by reverse transcription polymerase chain reaction (RT-PCR). Total cellular RNA was purified from cultured primary rat osteoblast cells and SaOS-2 cells by a modified method of single-step guanidinium thiocyanate-phenol-chloroform RNA extraction (Chomczynski and Sacchi (1987) Analyt. Biochem. 162:156–159; and Grey et al. (2001) Endocrinology 142:1098–1106). RNA concentration and purity were determined by measuring the optical density using a Gene Quant™ spectrophotometer (Pharmacia, Little Chalfont, UK) and the quality was determined by electrophoresis on a 1% agarose gel. RNA was treated with DNase and RT-PCR amplifications were carried out following the previously published protocol (Grey et al. (2001) Endocrinology 142: 1098–1106). PCR was performed in an automatic DNA thermal cycler (Mastercycler Personal, Eppendorf, Hamburg, Germany). After an initial denaturation step of 2 min at 94° C., 35 cycles of denaturing at 94° C. for 30 seconds, annealing at 56° C. for 30 seconds, and extension at 72° C. for 1 minute were performed. At the end of each set of cycles there was a final extension step at 72° C. for 15 minutes. PCR reaction products were visualized on a 1% TBE agarose gel. PCR products were purified from agarose gels using QIAquick gel extraction kit (Qiagen, Valencia, Calif.), and their sequences were determined on an ABI 377 XL DNA Sequencer (PE Biosystems, Foster City, Calif.). Control RT-PCR amplifications were carried out without reverse transcriptase.

Unexpectedly, LRP-1 was found to be expressed in both primary rat osteoblasts and SaOS-2 cells. LRP-2 was found to be expressed in primary rat osteoblasts but not in SaOS-2 cells. Lactoferrin has been identified as an osteoblast growth factor present in fractionated bovine milk. It stimulates proliferation of cultured osteoblastic cells of rat, mouse, and human origin potently and in a dose-dependent manner. Lactoferrin is also mitogenic to chondrocytes, and is capable of inducing osteoblast differentiation as well. It was found to significantly increase the number of mineralized bone nodules in long-term osteoblast cultures. Lactoferrin also inhibits apoptosis induced by serum withdrawal in primary rat osteoblasts. Lactoferrin strongly inhibits osteoclastogenesis in a murine bone marrow culture assay, but does not affect the bone-resorbing activity of mature osteoclasts. The ability of lactoferrin to induce osteoblast anabolism and inhibit osteoclast development in vitro suggests that it may be anabolic to bone in vivo. Indeed, when lactoferrin was administered to adult mice by unilateral local hemicalvarial injection, there were dose-dependent and substantial increases in indices of bone formation and bone area.

Interactions between Lactoferrin and LRP-1, LRP-2, and p42/44 MAP Kinase

Lactoferrin has been found to bind two endocytic members of the low-density lipoprotein receptor family, LRP-1 and LRP-2/megalin. LRP-1 and LRP-2 are both expressed in rodent osteoblastic cells, but only LRP-1 is expressed in SaOS-2 cells. It was observed under confocal microscopy that lactoferrin is endocytosed by primary rat osteoblastic cells, and that the LRP-1/2-specific inhibitor, receptor-associated protein (RAP), abrogates this process. Further, lactoferrin activates the p42/44 MAP kinase signaling pathway in osteoblastic cells. It was found that lactoferrin-induced osteoblast proliferation is inhibited by specific inhibitors of MAP kinase. Lactoferrin-induced osteoblast proliferation and MAP kinase phosphorylation are also blocked by RAP, implicating LRP-1/2 as mediators of the mitogenic effects of lactoferrin in osteoblasts. Moreover, lactoferrin induces proliferation in SaOS-2 cells. Lactoferrin-induced proliferation in LRP-1-null fibroblasts is substantially less marked than that observed in LRP-1+/+ cells. Taken together, these data demonstrate that lactoferrin is anabolic to bone, and that its growth-factor like effects on osteoblastic cells are mediated in a large part by LRP-1. This work provides further evidence for an important role of the LRP receptor family in regulation of bone growth.

The three dimensional structure of lactoferrin has revealed that it is subdivided into an N-lobe and a C-lobe, each binding one atom of iron. The N-lobe has been shown to have mitogenic effect near comparable to that of the full-length protein, suggesting that shorter polypeptides are potentially therapeutic. There is also possibility that, as lactoferrin is slowly broken down, latent activities in either lobe may emerge. Lactoferricin, a short N-terminal peptide of lactoferrin that has been shown to be effective in bacterial killing, had only a modest osteogenic effect. Transferrin also was not a potent mitogen on osteoblasts. When lactoferrin was stripped of iron and re-loaded with chromium or manganese ions, the osteogenic activity was similar to the iron-loaded molecule, implying that the iron itself is not crucial for the mitogenic activity of lactoferrin in osteoblasts.

Other Embodiments

All of the features disclosed in this specification can be combined in any combination. Each feature disclosed in this specification can be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of identifying a candidate compound for treating a bone condition, the method comprising:
   contacting a compound with a cell expressing an LRP-1 gene, and quantifying an expression level of the LRP-1 gene in the cell, wherein the expression level of the LRP-1 gene in the presence of the compound, if different from that in the absence of the compound, indicates that the compound is a candidate for treating a bone condition.

2. The method of claim 1, wherein the cell is an osteoblast cell, osteoblast-like cell, or osteocyte.

3. The method of claim 2, wherein the cell is a SaOS-2 cell.

4. The method of claim 1, wherein the cell is an osteoclast cell.

5. A method of identifying a candidate compound for treating a bone condition, the method comprising:
   contacting a compound with a cell expressing an LRP-1 gene encoding an LRP-1 protein, and quantifying an activity of the LRP-1 protein in the cell, wherein the activity of the LRP-1 protein in the presence of the compound, if different from that in the absence of the compound, indicates that the compound is a candidate for treating a bone condition.

6. The method of claim 5, wherein the cell is an osteoblast cell, osteoblast-like cell, or osteocyte.

7. The method of claim 6, wherein the cell is a SaOS-2 cell.

8. The method of claim 5, wherein the cell is an osteoclast cell.

* * * * *